US008927783B2

(12) United States Patent
Horton et al.

(10) Patent No.: US 8,927,783 B2
(45) Date of Patent: Jan. 6, 2015

(54) RECOVERING ETHANOL WITH SIDESTREAMS TO REGULATE $C_3+$ ALCOHOLS CONCENTRATIONS

(75) Inventors: Trinity Horton, Houston, TX (US); Radmila Jevtic, Pasadena, TX (US); Victor J. Johnston, Houston, TX (US); David Lee, Seabrook, TX (US); Adam Orosco, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 577 days.

(21) Appl. No.: 13/292,885

(22) Filed: Nov. 9, 2011

(65) Prior Publication Data

US 2012/0277488 A1 Nov. 1, 2012

Related U.S. Application Data

(63) Continuation-in-part of application No. 13/094,588, filed on Apr. 26, 2011, now Pat. No. 8,686,200, and a continuation-in-part of application No. 13/094,657, filed on Apr. 26, 2011, now Pat. No. 8,754,268.

(51) Int. Cl.
*C07C 29/149* (2006.01)
*C07C 29/80* (2006.01)
*C07C 51/12* (2006.01)

(52) U.S. Cl.
CPC ............... *C07C 51/12* (2013.01); *C07C 29/149* (2013.01); *C07C 29/80* (2013.01)
USPC ........................................................ 568/885

(58) Field of Classification Search
CPC .............................. C07C 29/149; C07C 29/80
USPC ........................................................ 568/885
See application file for complete search history.

(56) References Cited

U.S. PATENT DOCUMENTS

| | | |
|---|---|---|
| 2,649,407 A | 8/1953 | Harrison et al. |
| 2,702,783 A | 2/1955 | Harrison et al. |
| 2,801,209 A | 7/1957 | Muller et al. |
| 2,882,244 A | 4/1959 | Milton |
| 3,130,007 A | 4/1964 | Breck |
| 3,408,267 A | 10/1968 | Miller et al. |
| 3,445,345 A | 5/1969 | Katzen et al. |
| 3,478,112 A | 11/1969 | Karl et al. |
| 3,990,952 A | 11/1976 | Katzen et al. |
| 4,275,228 A | 6/1981 | Gruffaz et al. |
| 4,306,942 A | 12/1981 | Brush et al. |
| 4,317,918 A | 3/1982 | Takano et al. |
| 4,319,058 A | 3/1982 | Kulprathipanja et al. |
| 4,379,028 A | 4/1983 | Berg et al. |
| 4,395,576 A | 7/1983 | Kwantes et al. |
| 4,398,039 A | 8/1983 | Pesa et al. |
| 4,421,939 A | 12/1983 | Kiff et al. |
| 4,422,903 A | 12/1983 | Messick et al. |
| 4,454,358 A | 6/1984 | Kummer et al. |
| 4,465,854 A | 8/1984 | Pond et al. |
| 4,471,136 A | 9/1984 | Larkins et al. |
| 4,480,115 A | 10/1984 | McGinnis |
| 4,492,808 A | 1/1985 | Hagen et al. |
| 4,497,967 A | 2/1985 | Wan |
| 4,520,213 A | 5/1985 | Victor |
| 4,541,897 A | 9/1985 | Sommer et al. |
| 4,626,321 A | 12/1986 | Grethlein et al. |
| 4,678,543 A | 7/1987 | Houben et al. |
| 4,692,218 A | 9/1987 | Houben et al. |
| 4,777,303 A | 10/1988 | Kitson et al. |
| 4,804,791 A | 2/1989 | Kitson et al. |
| 4,842,693 A | 6/1989 | Wheldon |
| 4,961,826 A | 10/1990 | Grethlein et al. |
| 4,985,572 A | 1/1991 | Kitson et al. |
| 4,990,655 A | 2/1991 | Kitson et al. |
| 4,994,608 A | 2/1991 | Torrence et al. |
| 5,001,259 A | 3/1991 | Smith et al. |
| 5,026,908 A | 6/1991 | Smith et al. |
| 5,035,776 A | 7/1991 | Knapp |
| 5,061,671 A | 10/1991 | Kitson et al. |
| 5,124,004 A | 6/1992 | Grethlein et al. |
| 5,144,068 A | 9/1992 | Smith et al. |
| 5,149,680 A | 9/1992 | Kitson et al. |
| 5,185,481 A | 2/1993 | Muto et al. |
| 5,215,902 A | 6/1993 | Tedder |
| 5,227,141 A | 7/1993 | Kim et al. |
| 5,233,099 A | 8/1993 | Tabata et al. |
| 5,237,108 A | 8/1993 | Marraccini et al. |
| 5,250,271 A | 10/1993 | Horizoe et al. |
| 5,284,983 A | 2/1994 | Muto et al. |

(Continued)

FOREIGN PATENT DOCUMENTS

| | | |
|---|---|---|
| EP | 0104197 | 4/1984 |
| EP | 0137749 | 4/1985 |

(Continued)

OTHER PUBLICATIONS

International Preliminary Report on Patentability for PCT/US2011/060019 mailed Nov. 7, 2013.
International Search Report and Written Opinion mailed Apr. 19, 2012 in International Application No. PCT/US2011/060019.
Y. Zhu et al., "Techno-economic Analysis for the Thermochemical Conversion of Lignocellulosic Biomass to Ethanol via Acetic Acid Synthesis", Apr. 1, 2009, pp. 1-71 (80 Pages).
Zheng, et al. (2007). Preparation and catalytic properties of a bimetallic Sn—Pt complex in the supercages of NaY zeolite by use of surface organometallic chemistry, Applied Organometallic Chemistry, 21(10), 836-840.

(Continued)

*Primary Examiner* — Elvis O Price

(57) ABSTRACT

This invention relates to purification and/or recovery of ethanol from a crude ethanol product obtained from the hydrogenation of acetic acid. Separation and purification processes of a crude ethanol mixture are employed to allow recovery of ethanol and remove impurities. In particular, the process involves one or more sidestreams to regulate $C_3+$ alcohols concentration in the recovered ethanol.

10 Claims, 4 Drawing Sheets

(56) References Cited

U.S. PATENT DOCUMENTS

| | | | |
|---|---|---|---|
| 5,348,625 A | 9/1994 | Berg | |
| 5,415,741 A | 5/1995 | Berg | |
| 5,437,770 A | 8/1995 | Berg | |
| 5,445,716 A | 8/1995 | Berg | |
| 5,449,440 A | 9/1995 | Rescalli et al. | |
| RE35,377 E | 11/1996 | Steinberg et al. | |
| 5,599,976 A | 2/1997 | Scates et al. | |
| 5,762,765 A | 6/1998 | Berg | |
| 5,800,681 A | 9/1998 | Berg | |
| 5,821,111 A | 10/1998 | Grady et al. | |
| 5,993,610 A | 11/1999 | Berg | |
| 6,121,498 A | 9/2000 | Tustin et al. | |
| 6,143,930 A | 11/2000 | Singh et al. | |
| 6,232,352 B1 | 5/2001 | Vidalin | |
| 6,294,703 B1 | 9/2001 | Hara et al. | |
| 6,375,807 B1 | 4/2002 | Nieuwoudt et al. | |
| 6,509,180 B1 | 1/2003 | Verser et al. | |
| 6,627,770 B1 | 9/2003 | Cheung et al. | |
| 6,657,078 B2 | 12/2003 | Scates et al. | |
| 6,685,754 B2 | 2/2004 | Kindig et al. | |
| 6,693,213 B1 | 2/2004 | Kolena et al. | |
| 6,696,596 B1 | 2/2004 | Herzog et al. | |
| 6,723,886 B2 | 4/2004 | Allison et al. | |
| 6,755,975 B2 | 6/2004 | Vane et al. | |
| 6,906,228 B2 | 6/2005 | Fischer et al. | |
| 6,927,048 B2 | 8/2005 | Verser et al. | |
| 7,005,541 B2 | 2/2006 | Cheung et al. | |
| 7,074,603 B2 | 7/2006 | Verser et al. | |
| 7,115,772 B2 | 10/2006 | Picard et al. | |
| 7,208,624 B2 | 4/2007 | Scates et al. | |
| 7,297,236 B1 | 11/2007 | Vander Griend et al. | |
| 7,351,559 B2 | 4/2008 | Verser et al. | |
| 7,399,892 B2 | 7/2008 | Rix et al. | |
| 7,507,562 B2 | 3/2009 | Verser et al. | |
| 7,553,397 B1 | 6/2009 | Colley et al. | |
| 7,572,353 B1 | 8/2009 | Vander et al. | |
| 7,601,865 B2 | 10/2009 | Verser et al. | |
| 7,608,744 B1 | 10/2009 | Johnston et al. | |
| 7,682,812 B2 | 3/2010 | Verser et al. | |
| 7,732,173 B2 | 6/2010 | Mairal et al. | |
| 7,744,727 B2 | 6/2010 | Blum et al. | |
| 7,863,489 B2 | 1/2011 | Johnston et al. | |
| 7,884,253 B2 | 2/2011 | Stites et al. | |
| 7,888,082 B2 | 2/2011 | Verser et al. | |
| 2006/0019360 A1 | 1/2006 | Verser et al. | |
| 2006/0127999 A1 | 6/2006 | Verser et al. | |
| 2007/0270511 A1 | 11/2007 | Melnichuk et al. | |
| 2008/0135396 A1 | 6/2008 | Blum | |
| 2008/0193989 A1 | 8/2008 | Verser et al. | |
| 2009/0014313 A1 | 1/2009 | Lee et al. | |
| 2009/0023192 A1 | 1/2009 | Verser et al. | |
| 2009/0069609 A1 | 3/2009 | Kharas et al. | |
| 2009/0081749 A1 | 3/2009 | Verser et al. | |
| 2009/0166172 A1 | 7/2009 | Casey | |
| 2009/0281354 A1 | 11/2009 | Mariansky et al. | |
| 2009/0318573 A1 | 12/2009 | Stites et al. | |
| 2010/0029980 A1 | 2/2010 | Johnston et al. | |
| 2010/0029995 A1 | 2/2010 | Johnston et al. | |
| 2010/0030001 A1 | 2/2010 | Chen et al. | |
| 2010/0030002 A1 | 2/2010 | Johnston et al. | |
| 2010/0121114 A1 | 5/2010 | Johnston et al. | |
| 2010/0197485 A1 | 8/2010 | Johnston et al. | |
| 2010/0197985 A1 | 8/2010 | Johnston et al. | |
| 2011/0082322 A1 | 4/2011 | Jevtic et al. | |

FOREIGN PATENT DOCUMENTS

| | | |
|---|---|---|
| EP | 0167300 | 1/1986 |
| EP | 0456647 | 11/1991 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| WO | WO 83/03409 | 10/1983 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2010/055285 | 5/2010 |
| WO | WO 2011/140485 A1 | 11/2011 |

OTHER PUBLICATIONS

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Acala, et al., (2005). Experimental and DFT studies of the conversion of ethanol and acetic acid on PtSn-based catalysts, Journal of Physical Chemistry, 109(6), 2074-2085.

RECOVERING ETHANOL WITH SIDESTREAMS TO REGULATE $C_3+$ ALCOHOLS CONCENTRATIONS

CROSS REFERENCE TO RELATED APPLICATION

This application claims priority to U.S. application Ser. No. 13/094,588, filed on Apr. 26, 2011, and U.S. application Ser. No. 13/094,657, filed on Apr. 26, 2011, the entire contents and disclosures of which are incorporated herein by reference.

FIELD OF THE INVENTION

The present invention relates generally to processes for producing and recovering ethanol and, in particular, to processes for recovering ethanol from a crude product from acetic acid hydrogenation that contains $C_3+$ alcohols, e.g., heavy alcohols.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acids, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition, when conversion is incomplete, acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

U.S. Pat. No. 2,801,209 describes production of ethanol from olefin dehydration that uses sidestreams to remove oils that buildup in the columns while recovering ethanol.

Therefore, a need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising hydrogenating acetic acid in a reactor in the presence of a catalyst to form a crude ethanol product, separating at least a portion of the crude ethanol product in a first distillation column to yield a first residue comprising acetic acid and water, wherein a substantial portion of the water in the crude ethanol product that is fed to the column is removed in the first residue, a first distillate comprising ethanol, ethyl acetate and water, and one or more sidestreams comprising one or more $C_3+$ alcohols, removing water from at least a portion of the first distillate to yield an ethanol mixture stream comprising less than 10 wt. % water, and recovering ethanol from the ethanol mixture stream.

In a second embodiment, the present invention is directed to a process for producing ethanol, comprising hydrogenating acetic acid in a reactor in the presence of a catalyst to form a crude ethanol product, separating a portion of the crude ethanol product in a first distillation column to yield a first distillate comprising ethyl acetate and a first residue comprising one or more $C_2+$ alcohols, acetic acid and water, wherein a majority of ethanol in the crude ethanol product that is fed to the column is removed in the first residue, separating a portion of the first residue in a second distillation column to yield a second residue comprising acetic acid and water, a second distillate comprising ethanol, and one or more sidestreams comprising one or more $C_3+$ alcohols.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Figure 1:
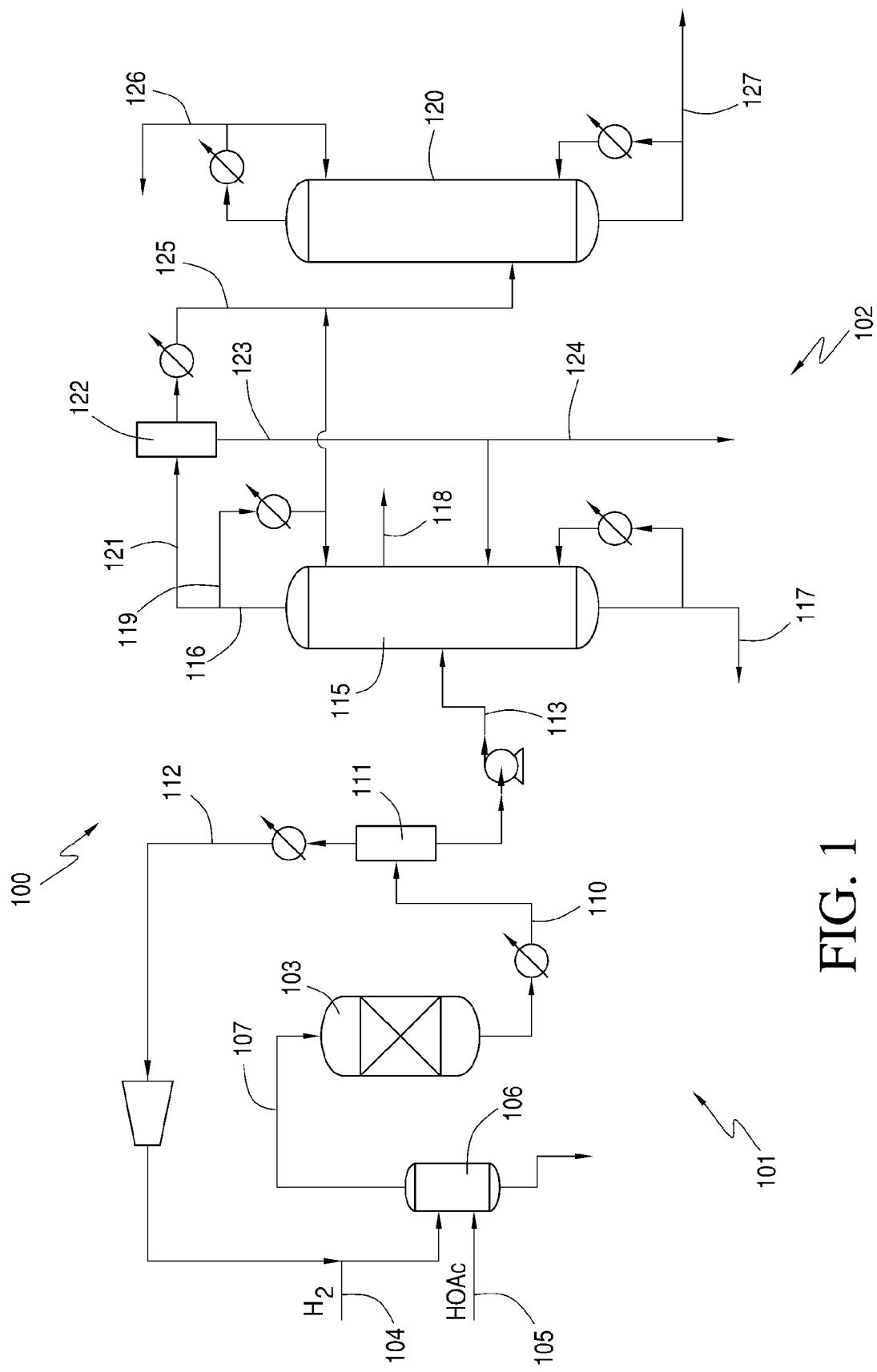
FIG. 1 is a schematic diagram of an ethanol production system having two columns with sidestreams to regulate $C_3+$ alcohols in the initial column in accordance with one embodiment of the present invention.

The present invention relates to processes for recovering ethanol produced by hydrogenating acetic acid in the presence of a catalyst. There may be additional components present during hydrogenation including acids, esters, aldehydes, and anhydrides, depending on the impurity level of the acetic acid feed. These impurities may be reduced along with acetic acid to produce $C_3+$ alcohols, e.g., heavy alcohols. In addition, side reactions during acetic acid hydrogenation may result in formation of $C_3+$ alcohols. The $C_3+$ alcohols may be formed in minor amounts, e.g., less than 10 wt. %, that when present are withdrawn with the recovered ethanol. This may lead to an ethanol product with levels of $C_3+$ alcohols impurities that may require further processing. The further processing may be inefficient to remove the minor amounts of the $C_3+$ alcohols from the ethanol. Although some $C_3+$ alcohols may be tolerated in certain ethanol applications, such as fuel grade ethanol, it is advantageous to regulate the $C_3+$ alcohols concentration in the recovered ethanol. Embodiments of the present invention overcome the problems associated with $C_3+$ alcohols by providing an efficient process to regulate the amount $C_3+$ alcohols in the recovered ethanol.

In particular, the present invention relates to recovering ethanol in less than two distillation columns so that the $C_3+$ alcohols do not build up in multiple columns. In one embodiment, the $C_3+$ alcohols are removed in the initial separation column via one or more sidestreams. In another embodiment, the $C_3+$ alcohols are initially concentrated in the residue along with ethanol and then separated via one or more sidestreams. In one embodiment, the residue comprises from 20 to 95 wt. % $C_2+$ alcohols, where of those $C_2+$ alcohols 90% to 99.9% are ethanol and from 0.01% to 10% are $C_3+$ alcohols. In preferred embodiments, the $C_2+$ alcohols composition comprises 95 to 99.9 wt. % ethanol and 0.01 to 5 wt. % $C_3+$ alcohols.

Higher alcohols such as $C_3+$ alcohols may be expected to be formed due to higher acids and/or esters in the feed. However, even in the absence of higher acids and/or esters, higher alcohols may be formed due to side reactions when hydrogenating acetic acid. These side reactions create capacity and purification inefficiencies in the separation system and may build up to unacceptable levels in the finished ethanol composition. The embodiments of the present invention advantageously reduce the $C_3+$ alcohol concentration in the finished ethanol composition.

$C_2+$ alcohols include ethanol and $C_3+$ alcohols. For purposes of the present invention, $C_3+$ alcohols are generally referred to as heavy alcohols and comprise alcohol species that generally have a higher boiling point than ethanol. These alcohols species may also include azeotropes of the $C_3+$ alcohols. The $C_3+$ alcohols have at least three carbons, e.g., at least four carbons or at least five carbons. In terms of ranges, $C_3+$ alcohols include from $C_3$ to $C_6$ alcohols, or more preferably from $C_3$ to $C_5$ alcohols. Examples of $C_3+$ alcohols include isopropanol, n-propanol, n-butanol, 2-butanol, isobutanol, tert-butanol, 2,2-dimethyl-1-propanol, 3-pentanol, 2-pentanol, 1-pentanol, 3-methyl-2-butanol, 2-methyl-2-butanol, mixtures thereof, and azeotropes thereof. In one embodiment, the $C_3+$ alcohols include isopropanol, n-propanol, n-butanol, and/or 2-butanol.

The separation of the crude ethanol product is controlled by thermodynamic phase equilibrium, which provides a concentration gradient throughout each column such that ethanol may be withdrawn overhead, and water and acetic acid may exit the bottom. However, when additional species, such as $C_3+$ alcohols and/or mixtures of $C_3+$ alcohols and ethyl acetate, are present in the column, a concentration gradient sufficient for separation may not exist, thereby causing the $C_3+$ alcohols to build up, e.g., bulge, at particular points within the column. In one embodiment, sidestreams of $C_3+$ alcohols may be taken in the liquid or vapor phase. In preferred embodiments, sidestreams are taken at locations in the column approximate to where the $C_3+$ alcohols build up. There may be multiple sidestreams to regulate the concentration of $C_3+$ alcohols.

Each of the $C_3+$ alcohols may build up at different points within the columns. In some embodiments, one of the heavy alcohols may build up and that location is selected for reducing the concentration of $C_3+$ alcohols. In particular 2-butanol or n-butanol may be used to determine where to withdraw the sidestreams.

In one embodiment, sidestreams remove the $C_3+$ alcohols such that distillate stream comprises less than 1000 wppm of $C_3+$ alcohols, e.g., less than 500 wppm or less than 400 wppm. In terms of ranges, the $C_3+$ alcohols concentration range in the distillate stream may be from 10 to 1000 wppm, e.g., from 10 to 500 wppm or from 10 to 400 wppm. In particular, the concentration of isopropanol, n-propanol, n-butanol, and/or 2-butanol in distillate stream may be less than 1000 wppm, e.g., less than 500 wppm or less than 400 wppm.

Optionally, an analyzer (not shown) may be used to measure the $C_3+$ alcohols concentration in the distillate stream and/or residue stream. When the analyzer measures that the concentration of the composition within column exceeds a target or specification level for the particular $C_3+$ alcohols, a signal may be provided and a sidestream may be taken from column to reduce the $C_3+$ alcohols concentration in the distillate and/or residue stream. For example, a target level of $C_3+$ alcohols concentration may be less than 1000 wppm, e.g., less than 500 wppm, or less than 400 wppm. One or more additional analyzers may also be used to measure the $C_3+$ alcohols concentration throughout the column.

In a first embodiment of the present invention, the process involves introducing the crude ethanol product to an initial separation column (first column), which separates the crude ethanol product into a distillate comprising ethanol, ethyl acetate and water, and a residue comprising water and unreacted acetic acid. One or more sidestreams are withdrawn from the first column to regulate $C_3+$ alcohol concentration. Water is then removed from the distillate to form an ethanol mixture stream, preferably comprising less than 10 wt. % water, less than 6 wt. % water or less than 4 wt. % water. In terms of ranges, the ethanol mixture stream comprises from 0.001 to 10 wt. % water, e.g., from 0.01 to 6 wt. % water or from 0.1 to 4 wt. % water. Product ethanol is then recovered from the ethanol mixture stream. Preferably, removing water in the distillate of the initial column and reducing the concentration of $C_3+$ alcohols may improve overall separation efficiency in recovering ethanol.

Water and ethanol form an azeotrope that is difficult to separate in a distillation column. The ethanol-water azeotrope limits the recoverable ethanol in distillation columns to an ethanol product comprising about 92-96 wt. % of ethanol. The energy required to approach this azeotrope in a distillation column, regardless of the presence of other compounds, is significant. The present invention involves using less energy in the initial column than would be required to approach the azeotrope, resulting in water being carried overhead in the distillate. Water is then removed from the distillate using a water separator, which beneficially requires less energy than is required for approaching the water/ethanol azeotrope in a distillation column. Thus, the present invention provides a low energy approach for dehydrating a crude ethanol product and thus removing water that is co-produced with ethanol.

The concentration of water in the distillate may vary depending on the acetic acid conversion. In one embodiment, the distillate comprises water in an amount greater than the amount of water in the ethanol/water azeotrope, e.g., in an amount greater than 4 wt. %, greater than 5 wt. %, or greater than 7 wt. %. In terms of ranges, the distillate optionally comprises water in an amount from 4 wt. % to 38 wt. %, e.g., from 7 wt. % to 32 wt. %, or from 7 wt. % to 25 wt. %.

Because the water concentration in the distillate is typically greater than the acceptable amount of water for industrial or fuel grade ethanol applications, in one embodiment of the present invention, the process involves removing a substantial portion of the water from the distillate to produce an ethanol mixture. Preferably, the water is removed before separating any appreciable amount of organics, ethyl acetate or acetaldehyde. In one embodiment, the water is removed prior to condensing the distillate. For example, distillate in vapor phase may be fed to an adsorption unit comprising a molecular sieve or a membrane. In some embodiments, distillate may be condensed to a liquid and fed to a membrane. The heat of vaporization for water is provided to the distillate to allow water to permeate through the membrane. In preferred embodiments, at least 50% of the water in the distillate is removed, e.g., at least 60% of the water or at least 75% of the water, based on the total amount of water in the distillate. In more preferred embodiments, from 90 to 99% of the water may be removed from the distillate. Thus, the resulting ethanol mixture may comprise only a minor amount of water, from 0.01 to 10 wt. %, e.g., from 0.5 to 6 wt. %, or from 0.5 to 4 wt. %. In one embodiment, the ethanol mixture comprises a water concentration that is less than the amount of water in the ethanol/water azeotrope. In order to achieve a water concentration that is below the amount of water in the ethanol/water azeotrope, a large of amount of energy is required. Thus, the present invention beneficially removes water from the first distillate to yield an ethanol mixture without a large amount of energy. Also, because the ethanol mixture comprises less water, the need to remove water during the later stage of product separation is also reduced.

In an exemplary embodiment, the energy requirements by the initial column in the process according to the present invention may be less than 5.5 MMBtu per ton of refined ethanol, e.g., less than 4.5 MMBtu per ton of refined ethanol or less than 3.5 MMBtu per ton of refined ethanol. In some embodiments, the process may operate with higher energy requirements provided that the total energy requirement is less than the energy required to remove most of the water from the crude ethanol product in the distillate, e.g. more than 65% of the water in the crude ethanol product.

The water that is removed from the distillate may be returned to the initial column and ultimately removed from the initial column via the residue. In one embodiment, a portion of the removed water may be condensed and returned below the feed point of the crude ethanol product to the initial column, e.g., near the bottom of the initial column. Depending on the water removal technique, there may be some ethanol and ethyl acetate in the removed water and thus it may be desirable to recover these compounds by returning at least a portion of the removed water to the initial column. Returning the removed water to the initial column may increase the amount of water withdrawn as the residue. In other embodiments, a portion of the removed water may be fed to a separation column, e.g. light-ends column, used in recovering an ethanol product from the ethanol mixture. The presence of a small amount of water, e.g., less than 10 wt. % water based on the total feed, in the light-ends column may be beneficial in facilitating the separation of ethyl acetate from ethanol. A portion of the removed water may also be purged as needed to remove water from the system.

The ethanol mixture may be further processed in the light-ends column to recover ethanol. In one embodiment, the $C_3+$ alcohols are removed prior to the light-ends column and there may be substantially no $C_3+$ alcohols in the light-ends column. In some embodiments, it may be desirable to maintain a concentration of water in the light-ends column. Depending on the type of water separator, the ethanol mixture may comprises less than 0.5 wt. % water. To control the water concentration, a by-pass line may be used to split the distillate. The split ratio may vary to control the amount of water in feed to the light-ends column. In one embodiment, the split ratio may range from 10:1 to 1:10, e.g., from 5:1 to 1:5 or about 1:1. Other split ratios may be used when controlling the water concentration. The distillate in the by-pass line is not separated to remove water and may be combined or co-fed with the ethanol mixture to the light-ends column. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %. The additional water for the light-ends column is typically recovered with the ethanol and separated as desired to provide an ethanol product.

The process of the present invention may use any suitable technique for removing water from the distillate. For example, water may be removed in the vapor phase, before condensation, or in the liquid phase. Water may be removed, for example, using an adsorption unit, membrane, molecular sieves, extractive column distillation, or a combination thereof. Suitable adsorption units include pressure swing adsorption (PSA) units and thermal swing adsorption (TSA) units. The adsorption units may comprises molecular sieves, such as aluminosilicate compounds.

A membrane or an array of membranes may also be employed to separate water from the distillate. The membrane or array of membranes may be selected from any suitable membrane that is capable of removing a permeate water stream from a stream that also comprises ethanol and ethyl acetate.

In a second embodiment, the process of recovering ethanol uses two distillation columns, in which the residue of the first column comprises a substantial portion of the ethanol, water, and the acetic acid from the crude ethanol product. The residue stream comprising ethanol, water, and acetic acid may be further separated to recover ethanol in a second column. In addition, the residue also comprises a substantial portion of the $C_3+$ alcohols. One or more sidestreams are withdrawn from the second column that separates the ethanol from acid acetic and water to regulate $C_3+$ alcohol concentration.

The residue stream from the first column, for example, may comprise at least 50% of the ethanol from the crude ethanol product, and more preferably at least 70%. In terms of ranges, the residue stream may comprise from 50% to 97.5% of the ethanol from the crude ethanol product, and more preferably from 70% to 97.5%. The amount of ethanol from the crude ethanol recovered in the residue may be greater than 97.5%, e.g. up to 99.9%, when the ethyl acetate concentration in the crude ethanol product is less than 2 wt. %. In some embodiments, depending on the ethyl acetate concentration, taking too much ethanol in the residue may cause undesirable leakage of ethyl acetate in the residue. It is preferred that ethyl acetate is not withdrawn in the residue and may be present in very low amounts, e.g., less than 100 wppm or less than 50 wppm.

The residue stream comprises a substantial portion of the water and the acetic acid from the crude ethanol product. The residue stream may comprise at least 80% of the water from the crude ethanol product, and more preferably at least 90%. In terms of ranges, the residue stream preferably comprises from 80% to 99.4% of the water from the crude ethanol product, and more preferably from 90% to 99.4%. The residue stream may comprise at least 85% of the acetic acid from the crude ethanol product, e.g., at least 90% and more preferably about 100%. In terms of ranges, the residue stream preferably comprises from 85% to 100% of the acetic acid from the crude ethanol product, and more preferably from 90% to 100%. In one embodiment, substantially all of the acetic acid is recovered in the residue stream.

In an exemplary embodiment, the energy requirements by the initial column in the process according to the present invention may be less than 5.5 MMBtu per ton of refined ethanol, e.g., less than 4.5 MMBtu per ton of refined ethanol or less than 3.5 MMBtu per ton of refined ethanol.

The distillate from the initial column comprises light organics, such as ethyl acetate and acetaldehyde. Removing these components from the crude ethanol product in the initial column provides an efficient means for removing light organics. In addition, the light organics are not carried over with the ethanol when multiple columns are used, thus reducing the formation of byproducts from the light organics. In one embodiment, the light organics are returned to the reactor, where the acetaldehyde and the ethyl acetate are converted to additional ethanol. In some embodiments, the light organics may be separated so that one stream comprising primarily acetaldehyde or ethyl acetate is returned to the reactor. In another embodiment, the light organics may be purged from the system.

Hydrogenation of Acetic Acid

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from other available carbon source. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also US Publ. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by converting carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The hydrogenation of acetic acid to form ethanol is preferably conducted in the presence of a hydrogenation catalyst. Suitable hydrogenation catalysts include catalysts comprising a first metal and optionally one or more of a second metal, a third metal or any number of additional metals, optionally on a catalyst support. The first and optional second and third metals may be selected from Group IB, IIB, IIIB, IVB, VB, VIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. In embodiments of the invention where the first metal comprises platinum, it is preferred that the catalyst comprises platinum in an amount less than 5 wt. %, e.g., less than 3 wt. % or less than 1 wt. %, due to the high commercial demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, in some embodiments of the present invention the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain NorPro. The Saint-Gobain NorPro SS61138 silica exhibits the following properties: contains approximately 95 wt. % high surface area silica; surface area of about 250 m$^2$/g; median pore diameter of about 12 nm; average pore volume of about 1.0 cm$^3$/g as measured by mercury intrusion porosimetry and a packing density of about 0.352 g/cm$^3$ (22 lb/ft$^3$).

A preferred silica/alumina support material is KA-160 silica spheres from Sud Chemie having a nominal diameter of about 5 mm, a density of about 0.562 g/ml, an absorptivity of about 0.583 g H$_2$O/g support, a surface area of about 160 to 175 m$^2$/g, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments of the present invention, the crude ethanol product produced by the hydrogenation process, before any subsequent processing, such as purification and separation, will typically comprise acetic acid, ethanol and water. Exemplary compositional ranges for the crude ethanol product are provided in Table 1. The "others" identified in Table 1 may include, for example, esters, ethers, aldehydes, ketones, alkanes, and carbon dioxide.

In one embodiment, the crude ethanol product comprises acetic acid in an amount less than 20 wt. %, e.g., less than 15 wt. %, less than 10 wt. % or less than 5 wt. %. In terms of ranges, the acetic acid concentration of Table 1 may range from 0.1 wt. % to 20 wt. %, e.g., 0.2 wt. % to 15 wt. %, from 0.5 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Ethanol Recovery

Figure 2:
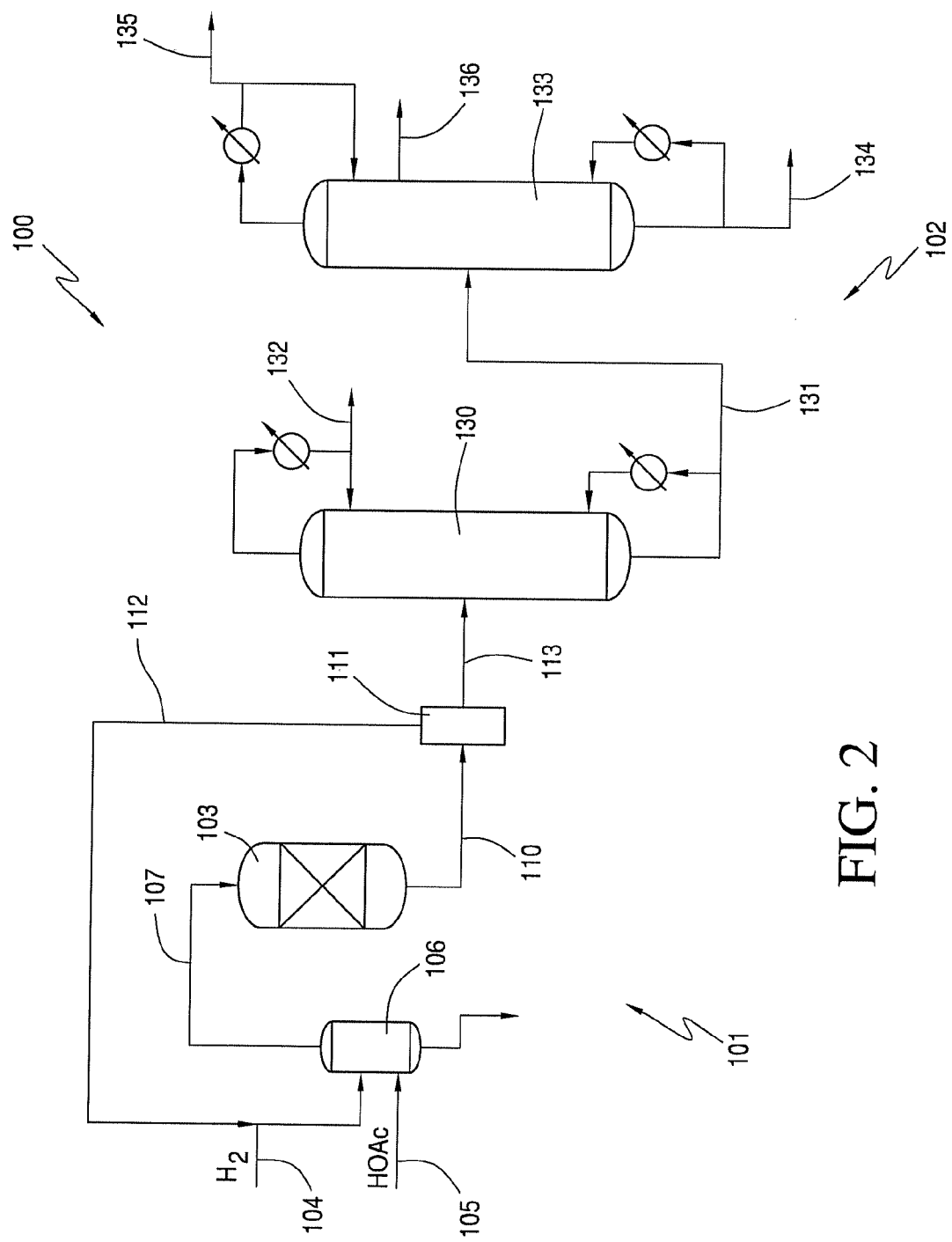
FIG. 2 is a schematic diagram of an ethanol production system having two columns with sidestreams to regulate $C_3+$ alcohols in the last column in accordance with one embodiment of the present invention.

The crude ethanol product containing $C_3+$ alcohols may be treated to control the amount of $C_3+$ alcohols in the ethanol product, as shown by exemplary hydrogenation systems 100 in FIGS. 1 and 2. Each hydrogenation system 100 provides a suitable hydrogenation reactor and a process for separating ethanol from the crude reaction mixture according to an embodiment of the invention. System 100 comprises reaction zone 101 and separation zone 102. Further modifications and additional components to reaction zone 101 and separation zone 102 are described below.

Reaction zone 101 comprises reactor 103, hydrogen feed line 104 and acetic acid feed line 105. Hydrogen and acetic acid are fed to a vaporizer 106 via lines 104 and 105, respectively, to create a vapor feed stream in line 107 that is directed to reactor 103. In one embodiment, lines 104 and 105 may be combined and jointly fed to the vaporizer 106. The temperature of the vapor feed stream in line 107 is preferably from 100° C. to 350° C., e.g., from 120° C. to 310° C. or from 150° C. to 300° C. Any feed that is not vaporized is removed from vaporizer 106, and may be recycled or discarded. In addition, although line 107 is shown as being directed to the top of reactor 103, line 107 may be directed to the side, upper portion, or bottom of reactor 103.

Reactor 103 contains the catalyst that is used in the hydrogenation of the carboxylic acid, preferably acetic acid. In one embodiment, one or more guard beds (not shown) may be used upstream of the reactor, optionally upstream of vaporizer 106, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product stream is withdrawn, preferably continuously, from reactor 103 via line 110.

The crude ethanol product stream may be condensed and fed to a separator 111, which, in turn, forms a vapor stream 112 and a liquid stream 113. In some embodiments, separator

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 70 | 15 to 60 | 20 to 50 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| $C_3+$ Alcohols | 0.0001 to 8 | 0.0001 to 1 | 0.0001 to 0.01 | — |
| Others | 0.1 to 10 | 0.1 to 6 | 0.1 to 4 | — |

111 may comprise a flasher or a knockout pot. The separator 111 may operate at a temperature of from 20° C. to 250° C., e.g., from 30° C. to 225° C. or from 60° C. to 200° C. The pressure of separator 111 may be from 50 kPa to 2000 kPa, e.g., from 75 kPa to 1500 kPa or from 100 kPa to 1000 kPa. Optionally, the crude ethanol product in line 110 may pass through one or more membranes to separate hydrogen and/or other non-condensable gases.

The vapor stream 112 exiting separator 111 may comprise hydrogen and hydrocarbons, and may be purged and/or returned to reaction zone 101. As shown, vapor stream 112 is combined with the hydrogen feed 104 and co-fed to vaporizer 106. In some embodiments, the returned vapor stream 112 may be compressed before being combined with hydrogen feed 104.

In FIG. 1, the liquid stream 113 from separator 111 is withdrawn and directed as a feed composition to the side of first distillation column 115, also referred to as an "acid-water column." In one embodiment, the contents of liquid stream 113 are substantially similar to the crude ethanol product obtained from the reactor, except that the composition has been depleted of hydrogen, carbon dioxide, methane or ethane, which have been removed by separator 106. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

COLUMN FEED COMPOSITION
(Liquid Stream 113)

| | Conc. (wt. %) | Conc. (wt. %) | Conc. (wt. %) |
|---|---|---|---|
| Ethanol | 5 to 70 | 10 to 60 | 15 to 50 |
| Acetic Acid | <90 | 5 to 80 | 15 to 70 |
| Water | 5 to 45 | 5 to 30 | 10 to 30 |
| Ethyl Acetate | <35 | 0.001 to 15 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| $C_3$+ Alcohols | <8 | <1 | <0.1 |
| Other Esters | <5 | <0.005 | <0.001 |
| Other Ethers | <5 | <0.005 | <0.001 |

The amounts indicated as less than (<) in the tables throughout the present specification are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. In should be understood that these other components may be carried through in any of the distillate or residue streams described herein and will not be further described herein, unless indicated otherwise.

Optionally, crude ethanol product in line 110 or in liquid stream 113 may be further fed to an esterification reactor, hydrogenolysis reactor, or combination thereof. An esterification reactor may be used to consume acetic acid present in the crude ethanol product to further reduce the amount of acetic acid to be removed. Hydrogenolysis may be used to convert ethyl acetate in the crude ethanol product to ethanol.

In FIG. 1, liquid stream 113 is fed to the first column 115 to yield a first distillate 116 and first residue 117. A sidestream 118 comprising $C_3$+ alcohols is also withdrawn from first column 115. Liquid stream 113 may be introduced in the middle or lower portion of first column 115. Sidestream 118 may be withdrawn above the fed point of liquid stream 113, preferably in the upper portion of first column 115, and below the reflux of the distillate. First column 115 may be tray column having from 1 to 150 trays, e.g., from 10 to 100 trays, from 20 to 95 trays or from 30 to 75 trays. For purposes of this invention, it is understood that tray 1 is the top tray. In one exemplary embodiment, first column 115 comprises 72 trays and sidestream 118 is withdrawn above the 30th tray, and more preferably between the 2nd and 25th tray. The location of the sidestream 118 may vary depending on the size of first column 115. In addition, although one sidestream 118 is shown in FIG. 1, it is understood that there may be multiple sidestreams.

In preferred embodiments, the $C_3$+ alcohols concentration in first distillate 116 is optimized using sidestream 118 to be within operating limits for ethanol standards, i.e. industrial ethanol standards or fuel ethanol standards, but in some embodiments it may be desirable to remove substantially all of the $C_3$+ alcohols from the first distillate in line 116. The concentration of $C_3$+ alcohols in a sidestream 118 may vary as necessary to control the $C_3$+ alcohols concentration in distillate and/or residue of column 115. For example, in some embodiments, a sidestream 118 may comprise up to 99 wt. % ethanol, ethyl acetate, and/or water, e.g., up to 95 wt. % or up to 90 wt. %, and less than 10 wt. % $C_3$+ alcohols, e.g., less than 5 wt. % or less than 1 wt. %.

In one embodiment, no entrainers are added to first column 115. Water and acetic acid, along with any other heavy components, if present, are removed from liquid stream 113 and are withdrawn, preferably continuously, as a first residue in line 117. Preferably, a substantial portion of the water in the crude ethanol mixture that is fed to first column 115 may be removed in the first residue, for example, up to about 75% or to about 90% of the water from the crude ethanol mixture. In one embodiment, 30 to 90% of the water in the crude ethanol mixture is removed in the residue, e.g., from 40 to 88% of the water or from 50 to 84% of the water.

When first column 115 is operated under about 170 kPa, the temperature of the residue exiting in line 117 preferably is from 90° C. to 130° C., e.g., from 95° C. to 120° C. or from 100° C. to 115° C. The temperature of the distillate exiting in line 116 preferably is from 60° C. to 90° C., e.g., from 65° C. to 85° C. or from 70° C. to 80° C. In some embodiments, the pressure of first column 115 may also range from 0.1 kPa to 510 kPa, e.g., from 1 kPa to 475 kPa or from 1 kPa to 375 kPa.

The first distillate in line 116 comprises some water in addition to ethanol and other organics. In terms of ranges, the water concentration in the first distillate in line 116 preferably is from 4 wt. % to 38 wt. %, e.g., from 7 wt. % to 32 wt. %, or from 7 to 25 wt. %. A portion of first distillate in line 119 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 115. The condensed portion of the first distillate may also be fed to a second column 120.

In some embodiments the first distillate may be split into equal portions, while in other embodiments, all of the first distillate may be condensed via line 119 or all of the first distillate may be processed in the water separation unit 122.

As shown, the remaining portion of the first distillate in line 121 is fed to a water separation unit 122. Water separation unit 122 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate.

In a preferred embodiment, water separator 122 is a pressure swing adsorption (PSA) unit. The PSA unit is optionally operated at a temperature from 30° C. to 160° C., e.g., from 80° C. to 140° C., and a pressure of from 0.01 kPa to 550 kPa, e.g., from 1 kPa to 150 kPa. The PSA unit may comprise from two to five beds. Water separator 122 may remove at least 95% of the water from the portion of first distillate in line 121, and more preferably from 99% to 99.99% of the water from the first distillate, in a water stream 123. All or a portion of water stream 123 may be returned to first column 115, where the water preferably is ultimately recovered in the first residue in line 117. Additionally or alternatively, all or a portion of water stream 123 may be removed from the hydrogenation system via line 124. The remaining portion of first distillate exits the water separator 122 as ethanol mixture stream 125. Ethanol mixture stream 125 may have a low water concentration of less than 10 wt. %, e.g., less than 6 wt. % or less than 2 wt. %.

Exemplary components of ethanol mixture stream 125 and first residue in line 117 are provided in Table 3 below. Preferably, there are no detectable amounts of $C_3+$ alcohols in the first residue. In addition, the concentration of $C_3+$ alcohols in the distillate is reduced and thus the concentration of $C_3+$ alcohols in ethanol mixture stream 125 is also reduced. It should also be understood that these streams may also contain other components, not listed, such as components derived from the feed.

TABLE 3

FIRST COLUMN WITH PSA (FIG. 1)

|  | Conc. (wt. %) | Conc. (wt. %) | Conc. (wt. %) |
|---|---|---|---|
| Ethanol Mixture Stream |  |  |  |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| $C_3+$ alcohols | <1 | 0.0001 to 0.5 | 0.005 to 0.4 |
| Residue |  |  |  |
| Acetic Acid | <90 | 1 to 50 | 2 to 35 |
| Water | 30 to 100 | 45 to 95 | 60 to 90 |
| Ethanol | <1 | <0.9 | <0.3 |

In an optional embodiment, all or a portion of either or both the first residue in line 117 and/or the separated stream in line 124 may be directed to the carbonylation system to serve as an extraction medium.

Preferably, ethanol mixture stream 125 is not returned or refluxed to first column 115 but rather the condensed portion of the first distillate in line 119 is refluxed. The condensed portion of the first distillate in line 119 may be combined with ethanol mixture stream 125 to control the water concentration fed to the second column 120. In FIG. 1, the condensed portion in line 123 and ethanol mixture stream 125 are co-fed to second column 120. In other embodiments, the condensed portion in line 123 and ethanol mixture stream 125 may be separately fed to second column 120. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

The second column 120 in FIG. 1, also referred to as the "light ends column," removes ethyl acetate and acetaldehyde from the first distillate in line 119 and/or ethanol mixture stream 125. Ethyl acetate and acetaldehyde are removed as a second distillate in line 126 and ethanol is removed as the second residue in line 127. Because C3+ alcohol concentrations have been reduced in first column 115 it may not be necessary to remove any sidestreams from second column 120. In an optional embodiment, ethanol may be removed from second column 120 in a sidestream and C3+ alcohols may be removed as the residue.

Second column 120 may be a tray column or packed column. In one embodiment, second column 120 is a tray column having from 5 to 120 trays, e.g., from 15 to 100 trays or from 20 to 90 trays. In one embodiment, second column 120 may operate at a pressure ranging from 0.1 kPa to 510 kPa, e.g., from 10 kPa to 450 kPa or from 50 kPa to 350 kPa. In one embodiment, it may be preferred to operate second column 120 at a pressure less than atmospheric pressure to decrease the energy required to separate ethyl acetate and ethanol. Although the temperature of second column 120 may vary, when at about 20 kPa to 70 kPa, the temperature of the second residue exiting in line 127 preferably is from 30° C. to 75° C., e.g., from 35° C. to 70° C. or from 40° C. to 65° C. The temperature of the second distillate exiting in line 126 preferably is from 20° C. to 55° C., e.g., from 25° C. to 50° C. or from 30° C. to 45° C.

The total concentration of water fed to second column 120 preferably is less than 10 wt. %, as discussed above. When first distillate in line 119 and/or ethanol mixture stream 125 comprises minor amounts of water, e.g., less than 1 wt. % or less than 0.5 wt. %, additional water may be fed to the second column 120 as an extractive agent in the upper portion of the column. A sufficient amount of water is preferably added via the extractive agent such that the total concentration of water fed to second column 120 is from 1 to 10 wt. % water, e.g., from 2 to 6 wt. %, based on the total weight of all components fed to second column 120. If the extractive agent comprises water, the water may be obtained from an external source or from an internal return/recycle line from one or more of the other columns or water separators.

Suitable extractive agents may also include, for example, dimethylsulfoxide; glycerine; diethylene glycol; 1-naphthol; hydroquinone; N,N'-dimethylformamide; 1,4-butanediol; ethylene glycol-1,5-pentanediol; propylene glycol-tetraethylene glycol-polyethylene glycol; glycerine-propylene glycol-tetraethylene glycol-1,4-butanediol; ethyl ether; methyl formate; cyclohexane; N,N'-dimethyl-1,3-propanediamine; N,N'-dimethylethylenediamine; diethylene triamine; hexamethylene diamine; 1,3-diaminopentane; an alkylated thiophene; dodecane; tridecane; tetradecane; chlorinated paraffins; or a combination thereof. When extractive agents are used, a suitable recovery system, such as a further distillation column, may be used to recycle the extractive agent.

The second distillate in line 126, which comprises ethyl acetate and/or acetaldehyde, preferably is refluxed as shown in FIG. 1, for example, at a reflux ratio of from 1:30 to 30:1, e.g., from 1:10 to 10:1 or from 1:3 to 3:1. In one aspect, not shown, the second distillate 126 or a portion thereof may be returned to reactor 103.

In one embodiment, the second distillate in line 126 and/or a refined second distillate, or a portion of either or both streams, may be further separated to produce an acetaldehyde-containing stream and an ethyl acetate-containing stream. For example, an additional column (not shown) may be used to separate second distillate in line 126. This may allow a portion of either the resulting acetaldehyde-containing stream or ethyl acetate-containing stream to be recycled to reactor 103 while purging the other stream. The purge stream may be valuable as a source of either ethyl acetate and/or acetaldehyde.

Exemplary components for the second distillate and second residue compositions for the second column 120 are provided in Table 4, below. It should be understood that the distillate and residue may also contain other components, not listed in Table 4.

TABLE 4

SECOND COLUMN (FIG. 1)

|  | Conc. (wt. %) | Conc. (wt. %) | Conc. (wt. %) |
|---|---|---|---|
| Second Distillate |  |  |  |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Second Residue |  |  |  |
| Ethanol | 80 to 99.5 | 85 to 97 | 60 to 95 |
| Water | <20 | 0.001 to 15 | 0.01 to 10 |
| Ethyl Acetate | <1 | 0.001 to 2 | 0.001 to 0.5 |
| Acetic Acid | <0.5 | <0.01 | 0.001 to 0.01 |
| $C_3$+ alcohols | <1 | 0.0001 to 0.5 | 0.005 to 0.4 |

Another exemplary two column separation scheme is shown in FIG. 2. Similar to FIG. 1, liquid stream 113 is obtained from reaction zone 101 and is introduced in the upper part of first column 130, e.g., upper half or upper third. For purposes of convenience, the columns in each exemplary separation process, may be referred as the first, second, etc., columns, but it is understood that first column 115 in FIG. 1 operates differently than the first column 130 of FIG. 2. In one embodiment, no entrainers are added to first column 130. In first column 130, a weight majority of the ethanol, water, acetic acid, and other heavy components, if present, are removed from liquid stream 113 and are withdrawn, preferably continuously, as the first residue in line 131. First column 130 also forms an overhead distillate, which is withdrawn in line 132, and which may be condensed and refluxed, for example, at a ratio of from 30:1 to 1:30, e.g., from 10:1 to 1:10 or from 1:5 to 5:1. The first distillate in line 132 preferably comprises a weight majority of the ethyl acetate from liquid line 113. In addition, distillate in line 132 may also comprise acetaldehyde.

As shown in FIG. 2, there are no sidestreams taken from first column 130 to reduce the concentration of heavy alcohols. In an optional embodiment, a sidestream comprising the weight majority of the ethanol, water, acetic acid may be withdrawn from a sidestream near the base of first column and C3+ alcohols removed as the residue.

When column 130 is operated under about 170 kPa, the temperature of the residue exiting in line 131 preferably is from 70° C. to 155° C., e.g., from 90° C. to 130° C. or from 100° C. to 110° C. The base of column 130 may be maintained at a relatively low temperature by withdrawing a residue stream comprising ethanol, water, and acetic acid, thereby providing an energy efficiency advantage. The temperature, at 170 kPa, of the distillate exiting in line 132 preferably is from 75° C. to 100° C., e.g., from 75° C. to 83° C. or from 81° C. to 84° C.

In one embodiment, column 130 of FIG. 2 may be operated at a temperature where most of the water, ethanol, and acetic acid are removed from the residue stream and only a small amount of ethanol and water is collected in the distillate stream due to the formation of binary and tertiary azeotropes. The weight ratio of water in the residue in line 131 to water in the distillate in line 132 may be greater than 1:1, e.g., greater than 2:1. The weight ratio of ethanol in the residue to ethanol in the distillate may be greater than 1:1, e.g., greater than 2:1.

The amount of acetic acid in the first residue may vary depending primarily on the conversion in reactor 103. In one embodiment, when the conversion is high, e.g., greater than 90%, the amount of acetic acid in the first residue may be less than 10 wt. %, e.g., less than 5 wt. % or less than 2 wt. %. In other embodiments, when the conversion is lower, e.g., less than 90%, the amount of acetic acid in the first residue may be greater than 10 wt. %.

The distillate preferably is substantially free of acetic acid, e.g., comprising less than 1000 wppm, less than 500 wppm or less than 100 wppm acetic acid. The distillate may be purged from the system or recycled in whole or part to reactor 103. In some embodiments, the distillate may be further separated into an acetaldehyde stream and an ethyl acetate stream. Either of these streams may be returned to the reactor 103 or separated from system as a separate product.

To recover ethanol, the residue in line 131 may be further separated in a second column 133, also referred to as an "acid separation column." An acid separation column may be used when the acetic acid concentration in the first residue is greater than 1 wt. %, e.g., greater than 5 wt. %. The first residue in line 131 is introduced to second column 133 preferably in the top part of column 133, e.g., top half or top third. Second column 133 yields a second residue in line 134 comprising acetic acid and water, and a second distillate in line 135 comprising ethanol.

A sidestream 136 comprising $C_3$+ alcohols is also withdrawn from second column 133. Sidestream 136 may be withdrawn above the feed point of first residue in line 131, preferably in the upper portion of second column 133, and below the reflux of the distillate. Second column 133 may be a tray column or packed column. Second column 133 may be a tray column having from 1 to 150 trays, e.g., from 10 to 100 trays, from 20 to 95 trays or from 30 to 75 trays. For purposes of this invention, it is understood that the tray 1 is the top tray. In one exemplary embodiment, second column 133 comprises 72 trays and sidestream 136 is withdrawn above the 20th tray, and more preferably between the 3nd and 15th tray. The location of the sidestream 136 may vary depending on the size of second column 133. In addition, although one sidestream 136 is shown in FIG. 2, it is understood that there may be multiple sidestreams.

In preferred embodiments, the $C_3$+ alcohols concentration in second distillate 135 is optimized using sidestream 136 to be within operating limits for ethanol standards, i.e. industrial ethanol standards or fuel ethanol standards, but in some embodiments it may be desirable to remove substantially all of the $C_3$+ alcohols from the second distillate in line 135. The concentration of $C_3$+ alcohols in a sidestream 136 may vary as necessary to control the $C_3$+ alcohols concentration in distillate and/or residue of column 133. For example, in some embodiments, a sidestream 136 may comprise up to 99 wt. % ethanol, ethyl acetate, and/or water, e.g., up to 95 wt. % or up to 90 wt. %, and less than 10 wt. % $C_3$+ alcohols, e.g., less than 5 wt. % or less than 1 wt. %.

Although the temperature and pressure of second column 133 may vary, when at atmospheric pressure the temperature of the second residue exiting in line 134 preferably is from 95° C. to 130° C., e.g., from 100° C. to 125° C. or from 110° C. to 120° C. The temperature of the second distillate exiting in line 136 preferably is from 60° C. to 105° C., e.g., from 75° C. to 100° C. or from 80° C. to 100° C. The pressure of second column 133 may range from 0.1 kPa to 510 kPa, e.g., from 1 kPa to 475 kPa or from 1 kPa to 375 kPa. Exemplary components for the distillate and residue compositions for second column 133 are provided in Table 5 below. It should be understood that the distillate and residue may also contain other components, not listed in Table 5.

TABLE 5

SECOND COLUMN (FIG. 2)

|  | Conc. (wt. %) | Conc. (wt. %) | Conc. (wt. %) |
|---|---|---|---|
| Second Distillate | | | |
| Ethanol | 70 to 99.9 | 75 to 98 | 80 to 95 |
| Ethyl Acetate | <10 | 0.001 to 5 | 0.01 to 3 |
| Acetaldehyde | <5 | 0.001 to 1 | 0.005 to 0.5 |
| Water | 0.1 to 30 | 1 to 25 | 5 to 20 |
| $C_3$+ alcohols | <1 | 0.0001 to 0.5 | 0.005 to 0.4 |
| Second Residue | | | |
| Acetic Acid | 0.1 to 45 | 0.2 to 40 | 0.5 to 35 |
| Water | 45 to 100 | 55 to 99.8 | 65 to 99.5 |
| Ethyl Acetate | <2 | <1 | <0.5 |
| Ethanol | <5 | 0.001 to 5 | <2 |

The remaining water from the second distillate in line 136 may be removed in further embodiments of the present invention. Depending on the water concentration, the ethanol product may be derived from the second distillate in line 136. Some applications, such as industrial ethanol applications, may tolerate water in the ethanol product, while other applications, such as fuel applications, may require an anhydrous ethanol. The amount of water in the distillate of line 136 may be closer to the azeotropic amount of water, e.g., at least 4 wt. %, preferably less than 20 wt. %, e.g., less than 12 wt. % or less than 7.5 wt. %. Water may be removed from the second distillate in line 136 using several different separation techniques as described herein. Particularly preferred techniques include the use of distillation column, membranes, adsorption units, and combinations thereof.

In one embodiment, any of the residue streams from FIGS. 1 and 2 may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor. The resulting water stream may be directed to a carbonylation system for use as an extractant as discussed above.

In other embodiments, for example, where the second residue comprises less than 50 wt. % acetic acid, possible options include one or more of: (i) neutralizing the acetic acid, or (ii) reacting the acetic acid with an alcohol. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

The columns shown in figures may comprise any distillation column capable of performing the desired separation and/or purification. For example, other than the acid columns describe above, the other columns preferably are a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

In accordance with various embodiments of the present invention, the $C_3$+ alcohols concentration in the finished ethanol composition is controlled within the limits for the particular application of the finished ethanol. In certain embodiments, the finished ethanol comprises less than 1000 wppm of $C_3$+ alcohols, e.g., less than 500 wppm or less than 400 wppm. For example, the amount of isopropanol in the finished ethanol may be from 80 to 1,000 wppm, e.g., from 95 to 1,000 wppm, from 100 to 700 wppm, or from 150 to 500 wppm. In particular, one or more sidestreams may reduce isopropanol concentrations in distillate that exceed 1000 wppm. In preferred embodiments, one or more sidestreams are positioned at a point(s) approximate to where isopropanol, n-propanol, n-butanol, and/or 2-butanol build up within the column.

After using a sidestream to reduce the concentration of $C_3$+ alcohols, the finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm.

The final ethanol product produced by the processes of the present invention may be taken from a stream that primarily comprises ethanol from exemplary systems shown in the figures. The ethanol product may be an industrial grade ethanol comprising from 75 to 96 wt. % ethanol, e.g., from 80 to 96 wt. % or from 85 to 96 wt. %, based on the total weight of the ethanol product. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 5, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entireties of which are incorporated herein by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, an example is provided below. It should be understood that this example is for illustrative purposes only and is not to be construed as limiting the invention in any manner.

EXAMPLE

The following examples were prepared with ASPEN Plus 7.1 simulation software to test various feed composition and separation systems.

Figure 3:
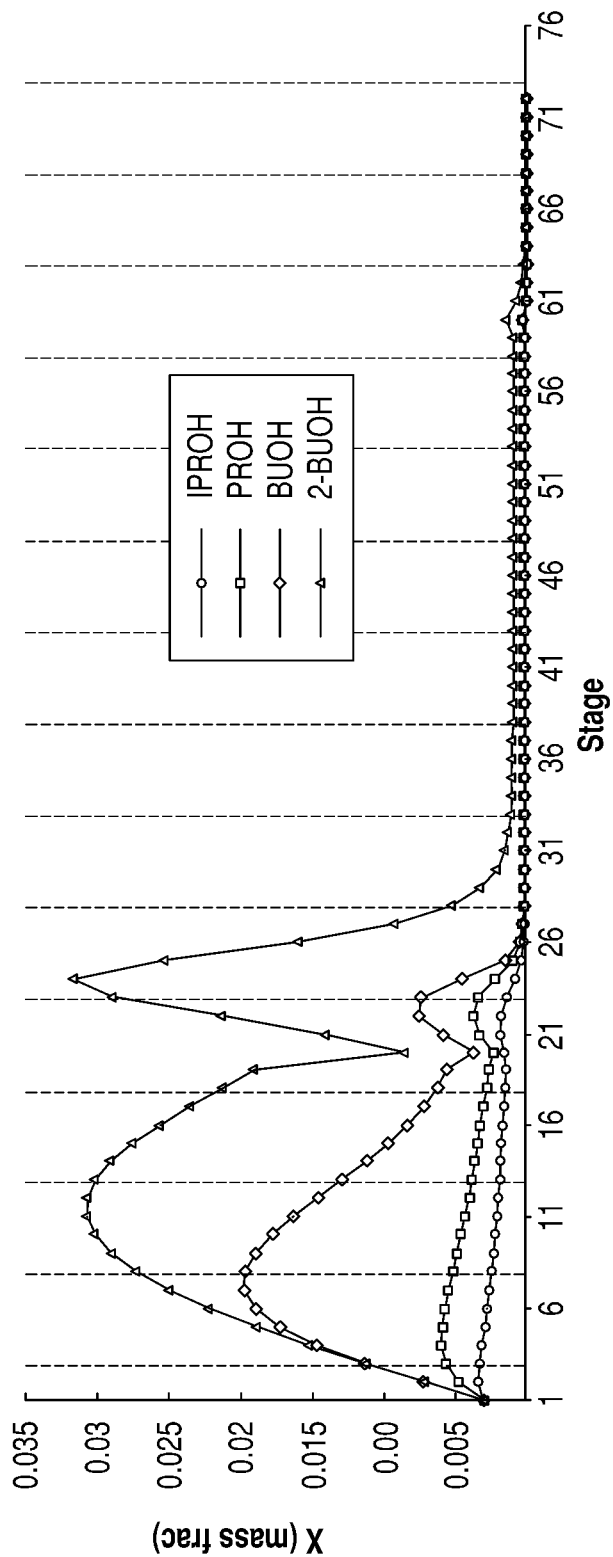
FIGS. 3 and 4 are graphical simulations illustrating the reduction of $C_3+$ alcohols bulging as a result of the addition of sidestreams in accordance with various embodiments of the present invention.
Figure 4:
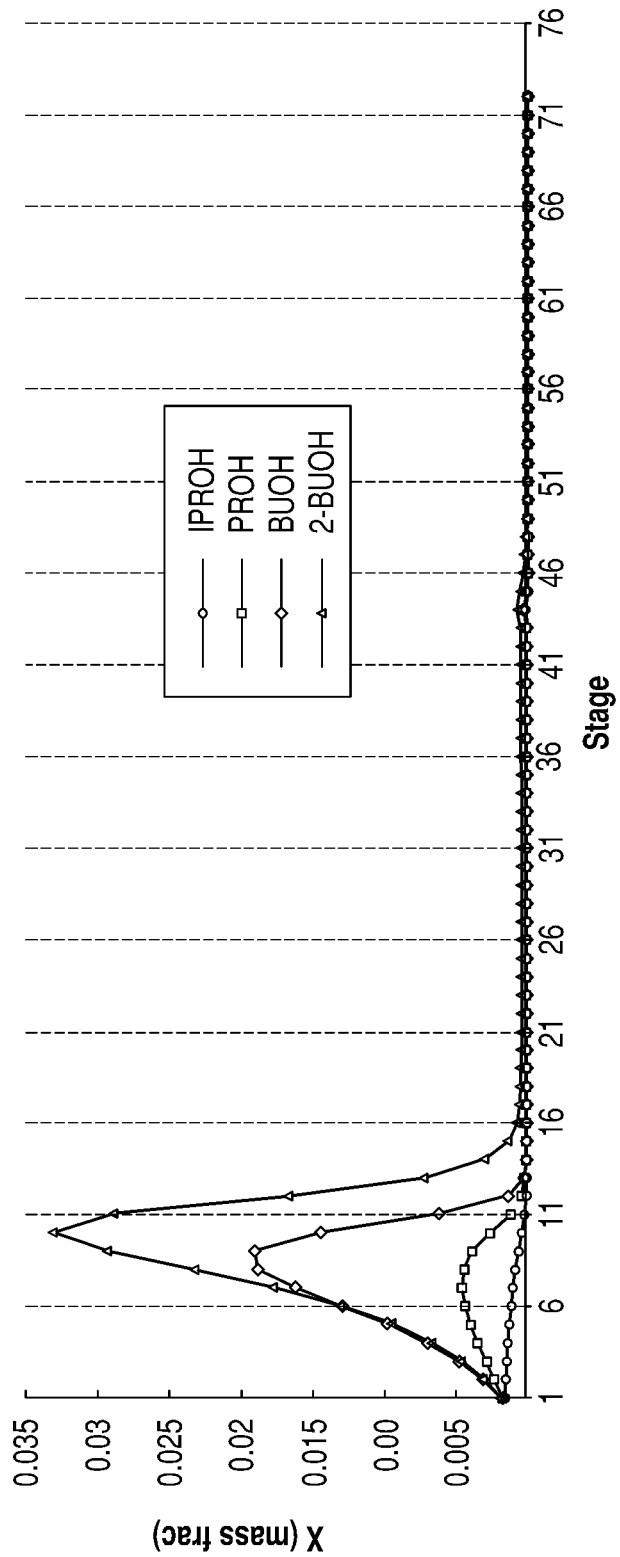

FIGS. 3 and 4 demonstrate bulging of $C_3$+ alcohols within columns. FIG. 3 shows a bulge in a first column of separation system shown in FIG. 1. FIG. 4 shows a bulge in a second column of separation system shown in FIG. 2. To reduce the concentration of $C_3$+ alcohols, one or more sidestreams may be taken at trays 12 and 23 in FIG. 3, and at tray 10 in FIG. 4.

While the invention has been described in detail, modifications within the spirit and scope of the invention will be readily apparent to those of skill in the art. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with one or more other embodiments, as will be appreciated by one of skill in the art. Furthermore, those of ordinary skill in the art will appreciate that the foregoing description is by way of example only, and is not intended to limit the invention.

We claim:

1. A process for producing ethanol, comprising:
hydrogenating acetic acid in a reactor in the presence of a catalyst to form a crude ethanol product;
separating a portion of the crude ethanol product in a first distillation column to yield a first distillate comprising ethyl acetate and a first residue comprising one or more $C_2$+ alcohols, acetic acid and water, wherein a majority of ethanol in the crude ethanol product that is fed to the column is removed in the first residue; and
separating a portion of the first residue in a second distillation column to yield a second residue comprising acetic acid and water, a second distillate comprising ethanol, and one or more sidestreams comprising one or more $C_3$+ alcohols.

2. The process of claim 1, wherein said one or more $C_2+$ alcohols are selected from the group consisting of ethanol, isopropanol, n-propanol, n-butanol, 2-butanol, isobutanol, tert-butanol, 2,2-dimethyl-1-propanol, 3-pentanol, 2-pentanol, 1-pentanol, 3-methyl-2-butanol, 2-methyl-2-butanol, a mixture thereof, and an azeotrope thereof.

3. The process of claim 1, wherein said first residue comprises said one or more $C_2+$ alcohols in an amount from 20 to 95 wt. % and, wherein said one or more $C_2+$ alcohols comprises from 90 to 99.9 wt. % ethanol and from 0.001 to 10 wt. % of said one or more $C_3+$ alcohols.

4. The process of claim 1, wherein said one or more $C_3+$ alcohols are selected from the group consisting of isopropanol, n-propanol, n-butanol, 2-butanol, isobutanol, tert-butanol, 2,2-dimethyl-1-propanol, 3-pentanol, 2-pentanol, 1-pentanol, 3-methyl-2-butanol, 2-methyl-2-butanol, a mixture thereof, and an azeotrope thereof.

5. The process of claim 1, wherein said one or more sidestreams comprise one or more $C_3$ to $C_6$ alcohols, a mixture thereof, and an azeotrope thereof.

6. The process of claim 1, wherein the second distillate comprises substantially none of said one or more $C_3+$ alcohols.

7. The process of claim 1, wherein the second distillate comprises less than 1000 wppm of said one or more $C_3+$ alcohols.

8. The process of claim 1, wherein at least 70% of the ethanol in the crude ethanol product is removed in the first residue stream.

9. The process of claim 1, further comprising reducing the water content of the second distillate to yield an ethanol product stream with reduced water content.

10. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

* * * * *